(12) United States Patent
Subramanian et al.

(10) Patent No.: US 11,551,819 B2
(45) Date of Patent: Jan. 10, 2023

(54) CONTACT TRACING AS A SERVICE USING A DATABASE SYSTEM

(71) Applicant: Salesforce.com, Inc., San Francisco, CA (US)

(72) Inventors: Balakrishnan Subramanian, San Francisco, CA (US); Simon Smith, San Francisco, CA (US); Bethany Pickard, San Francisco, CA (US); Yuhuan Tang, San Francisco, CA (US); Ruchika Mittal, San Francisco, CA (US); Emad Salman, San Francisco, CA (US); Sriram Gopalan, Foster City, CA (US)

(73) Assignee: salesforce.com, inc., San Francisco, CA (US)

( * ) Notice: Subject to any disclaimer, the term of this patent is extended or adjusted under 35 U.S.C. 154(b) by 10 days.

(21) Appl. No.: 16/944,644

(22) Filed: Jul. 31, 2020

(65) Prior Publication Data

US 2022/0037032 A1  Feb. 3, 2022

(51) Int. Cl.
*G16H 50/80* (2018.01)
*G06F 16/9032* (2019.01)
*G16H 50/70* (2018.01)
*G16H 50/30* (2018.01)
*H04W 4/029* (2018.01)

(52) U.S. Cl.
CPC ....... *G16H 50/80* (2018.01); *G06F 16/90332* (2019.01); *G16H 50/30* (2018.01); *G16H 50/70* (2018.01); *H04W 4/029* (2018.02)

(58) Field of Classification Search
CPC .......................... H04Q 4/029; G06F 16/90332
See application file for complete search history.

(56) References Cited

U.S. PATENT DOCUMENTS

| | | | |
|---|---|---|---|
| 8,548,940 B1 | 10/2013 | Rajaram et al. | |
| 8,645,341 B2 | 2/2014 | Salman | |
| 10,482,425 B2 | 11/2019 | Bezar et al. | |
| 10,701,054 B2 | 6/2020 | Padmanabhan et al. | |
| 2008/0300922 A1* | 12/2008 | Forgue | G16H 40/67 705/3 |
| 2019/0038225 A1* | 2/2019 | Leavitt | A61B 5/1122 |
| 2019/0180746 A1* | 6/2019 | Diwan | G10L 15/22 |
| 2020/0065764 A1 | 2/2020 | Bezar et al. | |
| 2021/0058736 A1* | 2/2021 | Ghazzaoui | G08B 21/0277 |
| 2021/0313074 A1* | 10/2021 | Mesirow | G16H 10/40 |
| 2021/0313075 A1* | 10/2021 | McNamara | G08B 21/22 |
| 2021/0358639 A1* | 11/2021 | Long | H04L 67/125 |
| 2022/0157473 A1* | 5/2022 | Marinescu | G06F 16/9024 |

FOREIGN PATENT DOCUMENTS

WO    2019152750 A1    8/2019

* cited by examiner

*Primary Examiner* — Robert A Sorey
(74) *Attorney, Agent, or Firm* — Polygon IP, LLP

(57) ABSTRACT

One or more enrollment messages may be received via a communication message. The enrollment messages may include identification information associated with a designated person, health status information indicating the presence or absence of one or more medical symptoms associated with the designated person, and contact information identifying one or more individuals with which the designated person has recently come into physical proximity. A visual representation of a contact tracing graph may be generated for presentation on a user interface.

20 Claims, 15 Drawing Sheets

(9 of 15 Drawing Sheet(s) Filed in Color)

CONTACT TRACING AS A SERVICE USING A DATABASE SYSTEM

COPYRIGHT NOTICE

A portion of the disclosure of this patent document contains material which is subject to copyright protection. The copyright owner has no objection to the facsimile reproduction by anyone of the patent document or the patent disclosure as it appears in the United States Patent and Trademark Office patent file or records but otherwise reserves all copyright rights whatsoever

FIELD OF TECHNOLOGY

This patent document relates generally to database systems and more specifically to the representation of interpersonal contacts in a database system.

BACKGROUND

"Cloud computing" services provide shared resources, applications, and information to computers and other devices upon request. In cloud computing environments, services can be provided by one or more servers accessible over the Internet rather than installing software locally on in-house computer systems. Users can interact with cloud computing services to undertake a wide range of tasks.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The included drawings are for illustrative purposes and serve only to provide examples of possible structures and operations for the disclosed inventive systems, apparatus, methods and computer program products for contact tracing. These drawings in no way limit any changes in form and detail that may be made by one skilled in the art without departing from the spirit and scope of the disclosed implementations.

DETAILED DESCRIPTION

Figure 1:
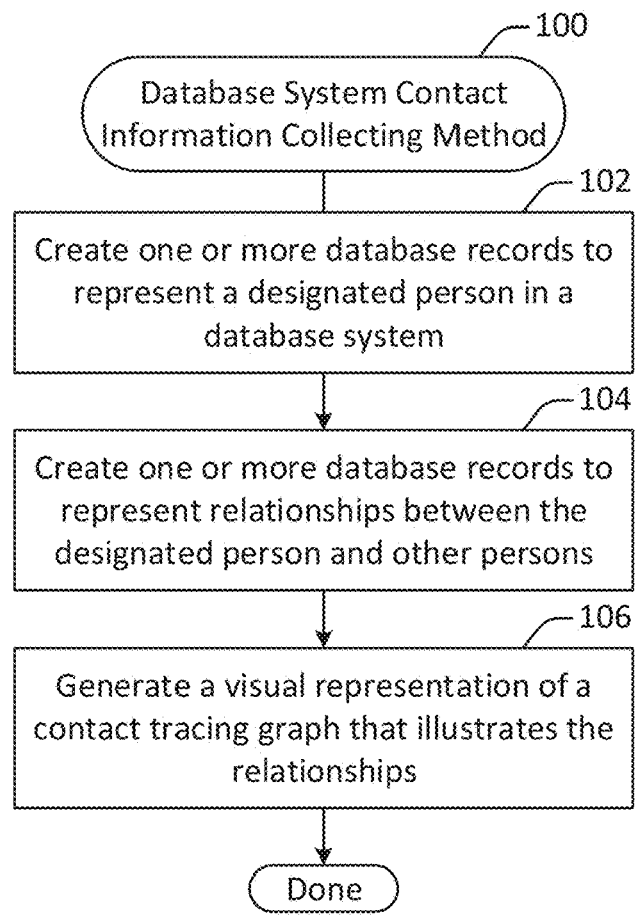
FIG. 1 illustrates an example of a method for collecting contact information in a database system performed in accordance with one or more embodiments.

Contact tracing presents a difficult problem for organizations. On one hand, tracing physical contacts between people can be a crucial component in a strategy to control the spread of a disease such as Covid-19 or seasonal influenza. On the other hand, privacy regulations require sensitive data to be handled securely and used only in particular ways. Further, concerns about privacy lead many individuals to avoid disclosing public health information that is necessary to improve public health outcomes.

In some contexts, contact tracing is performed in a unified manner by a centralized government. However, in many contexts public health responses are less organized and centralized contact tracing is absent or lacking. Further, even in the presence of centralized contact tracing additional contact tracing by organizations is vital for providing supplemental benefits to public health. For example, organizations such as state governments, county governments, or companies may wish to provide localized contact tracing that is specific to a location or an organizational context.

Organizations are often ill equipped to handle sensitive public health information, much less trace physical contacts revealed by the disclosure of public health information. Moreover, organizations may be limited by law in terms of the sensitive health information that they are allowed to collect, and yet may be unfamiliar with the details of such regulations.

Another difficulty with contact tracing is that many organizations rarely need to trace contacts or collect health information. However, when contact tracing does become necessary, the organization must quickly activate and scale the contact tracing capability if public health outcomes are to be improved.

According to various embodiments, techniques and mechanisms described herein provide for the secure collection, storage and utilization of public health information in a database system, along with the accurate and efficient use of such information to trace physical connections between people. In this way, a public or private organization may access contact tracing as a service via the internet. The service may be activated and scaled up on-demand, and later deactivated or scaled down when no longer needed. Further, the service may be configured so that individuals who are not public health experts may easily perform contact tracing tasks such as collecting health information and contacting individuals who may have been exposed to a disease.

Consider the situation of Alexandra, who works for Acme Corp. When a pandemic suddenly arises, Alexandra is tasked with managing Acme's response. Alexandra is not a doctor, however, and is unsure what information can be collected from Acme's employees, how to manage the information that is collected, and how to use that information to keep Acme's employees safe and the company as functional as possible. Using techniques and mechanisms described herein, Alexandra may quickly activate a contact tracing service that is specific to Acme. Alexandra may then recruit contact tracers from inside or outside Acme to assist in the contact tracing effort. Individuals can report their health information to one of these contact tracers, who can enter the information in the system. The service can guide the contact tracers to collect only the information that is legal to collect and that is helpful in performing contact tracing. The service can also guide the contact tracers in the identification, characterization, and tracing of physical contacts between individuals. Thus, the contact tracing service can allow Alexandra to help keep Acme's employees safe while at the same time facilitating in-person interactions between employees.

FIG. 1 illustrates an example of a method 100 for collecting contact information in a database system, performed in accordance with one or more embodiments. According to various embodiments, the method 100 may be performed at one or more systems within an on-demand computing services environment, such as the systems and environments shown in FIGS. 9-11.

One or more database records are created at 102 to represent a designated person in a database system. According to various embodiments, each person may be associated with one or more database records that include identification information, health information, and other such data. For example, information such as age, employment status, profession, and disease exposure status may be collected. Some such information may be static, while other such information may change over time. The creation of one or more database records to represent a designated person a database system is discussed in further detail with respect to the method 200 shown in FIG. 2.

One or more database records are created at 104 to represent interactions between the designated person and other persons. In some implementations, each interaction may be characterized. For example, an interaction may be classified as a family interaction, as physical contact, or as a designated degree of physical proximity. Additional details regarding the creation of database records representative of relations are described with respect to the method 300 shown in FIG. 3.

A visual representation of a contact tracing graph that illustrates the interactions is generated at 106. According to various embodiments, a contact tracing graph may include nodes that each represent individuals. Interactions between the individuals may be represented by linkages between the nodes. The generation of a contact tracing graph is described in further detail in reference to FIG. 3.

Figure 2:
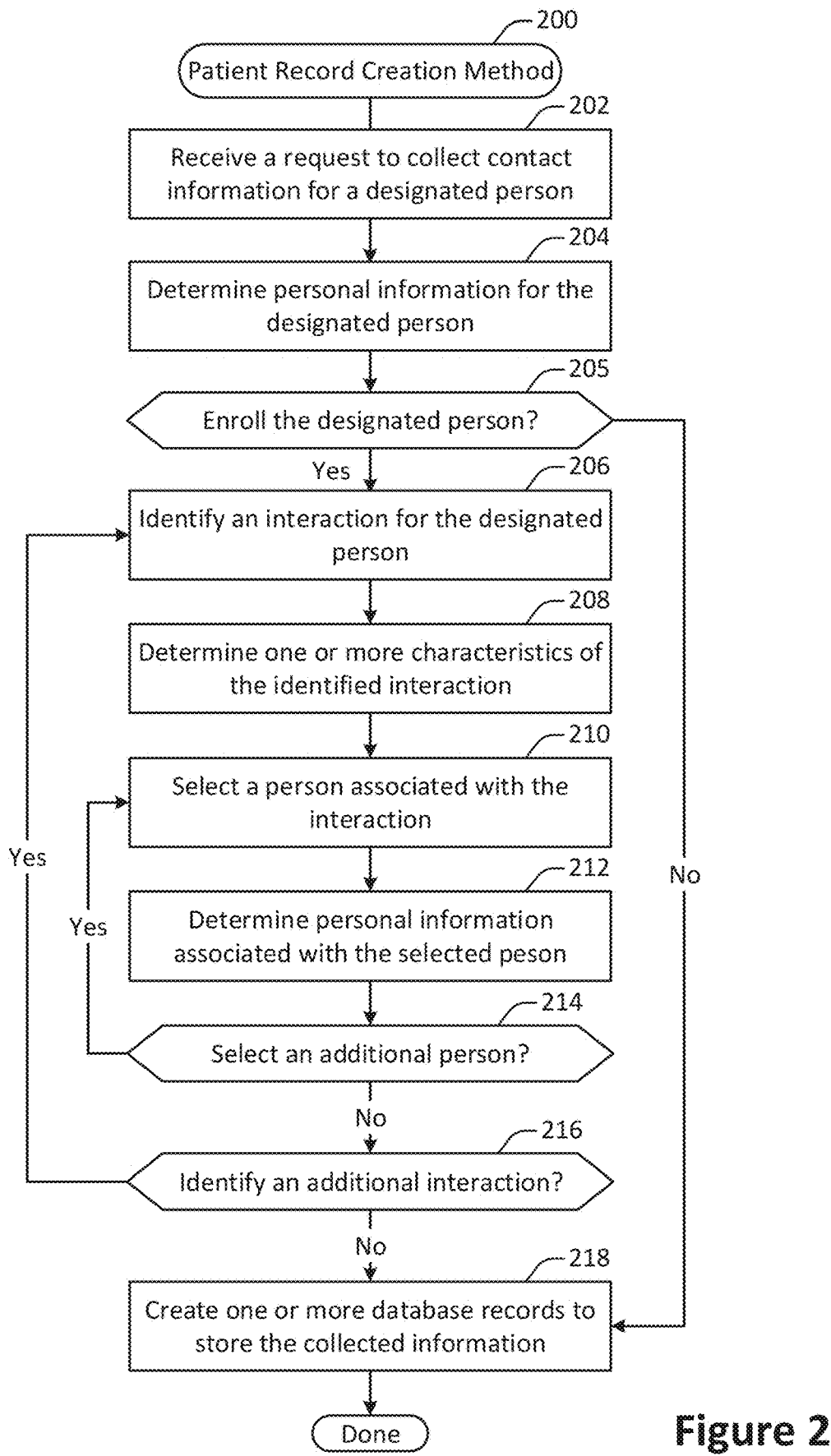
FIG. 2 illustrates an example of a method for creating a patient record performed in accordance with one or more embodiments.

FIG. 2 illustrates an example of a method 200 for creating a patient record, performed in accordance with one or more embodiments. According to various embodiments, the method 100 may be performed at one or more systems within an on-demand computing services environment, such as the systems and environments shown in FIGS. 9-11.

A request to collect contact information for a designated person is received at 202. In some implementations, the request may be generated by the system itself, by a contact tracer, or by a potential patient. For example, a person may call a contact number and self-report symptoms of an illness. As another example, the system may determine that a particular person should be enrolled. For instance, a company may automatically enroll particular types of employees. As yet another example, a contact tracer may contact a person as part of a contact tracing operation, as discussed with respect to the method 300 shown in FIG. 3.

A determination is made at 205 as to whether to enroll the designated person. In some embodiments, the determination may be made at least in part based on a clinical assessment. For example, if the person reports symptoms that are consistent with a medical problem, then the person may be enrolled. As another example, if the person reports a positive test for a targeted medical problem, then the person may be enrolled.

In some embodiments, the determination may be made at least in part based on a business judgment rule. For instance, a person may be enrolled if the person has been in direct contact with an individual known to have been infected.

Personal information for the designated person is determined at 204. In some implementations, personal information may be gathered by a contact tracer communicating with the designated person, for instance via a telephone call, text messaging session, or one or more emails. The contact tracer may follow a script to elicit particular information from the designated person.

In some embodiments, personal information may be gathered in part by natural language processing. For example, one or more recorded voice messages, telephone calls, text messages, or emails may be analyzed to identify personal information about the designated person. As another example, a chat bot may interact with a user via text messages.

In some embodiments, personal information may include household information. For instance, a person may provide contact and/or identification details for one or more members of the designated person's household.

In particular embodiments, a new person may be enrolled in the system only after a determination is made that the person is at risk of or exhibits symptoms of a particular illness, such as Covid-19. For instance, a person's symptoms may be evaluated to determine whether the person is likely to have the illness. If so, the person may be enrolled and recommended for testing.

According to various embodiments, the personal information may include any or all of a wide variety of information about the designated person. For example, the personal information may include identification information such as name, social security number, driver's license number, employee identification number, or other identification number. As another example, the personal information may include contact information such as one or more email addresses, phone numbers, residential addresses, mailing addresses, or zip codes. As yet another example, the personal information may include employment information such as employment status, employer identification information, office desk location, office building, office floor, or job title.

In some implementations, medical information may be collected. Medical information may include but is not limited to: age, weight one or more symptoms, one or more medical conditions, one or more medical interactions, and/or any other suitable information. Medical symptoms may include, for instance, the presence of a cough or a fever. Medical conditions may be self-reported or may be inferred from the medical symptoms. For example, a person may self-report as having diabetes. As another example, a person may report symptoms such as body aches and a fever, which the system, contact tracer, or other decision maker may use to infer the presence of an illness such as the seasonal influenza.

In particular embodiments, medical conditions may be qualified based on the available evidence. For instance, a positive test for a medical condition may cause the condition to be listed for the designated person with certainty, while a constellation of symptoms may cause the condition to be listed for the designated person with some probability indicator such as "possible seasonal influenza."

In particular embodiments, medical interaction information may identify actions such as doctor visits, hospital visits, tests administered, test results received. Such information may be provided by the designated person or may be retrieved from a remote database.

According to various embodiments, any or all of the personal information may be provided directly by the designated person. Alternative, any or all of the personal information may be retrieved from a database or remote computing system. For instance, a person's employee identification number or medical record identifier may be used to query a system to retrieve relevant information.

In particular embodiments, the personal information collected by depend on the context in which contact tracing is employed. For instance, a government agency may be authorized to collect a wide range of personal health information about a person, while an employer may be authorized to collect a more limited amount of health-related information. Such restrictions may be adhered to by tailoring the contact tracing service to the context in which it is employed.

Figure 4:
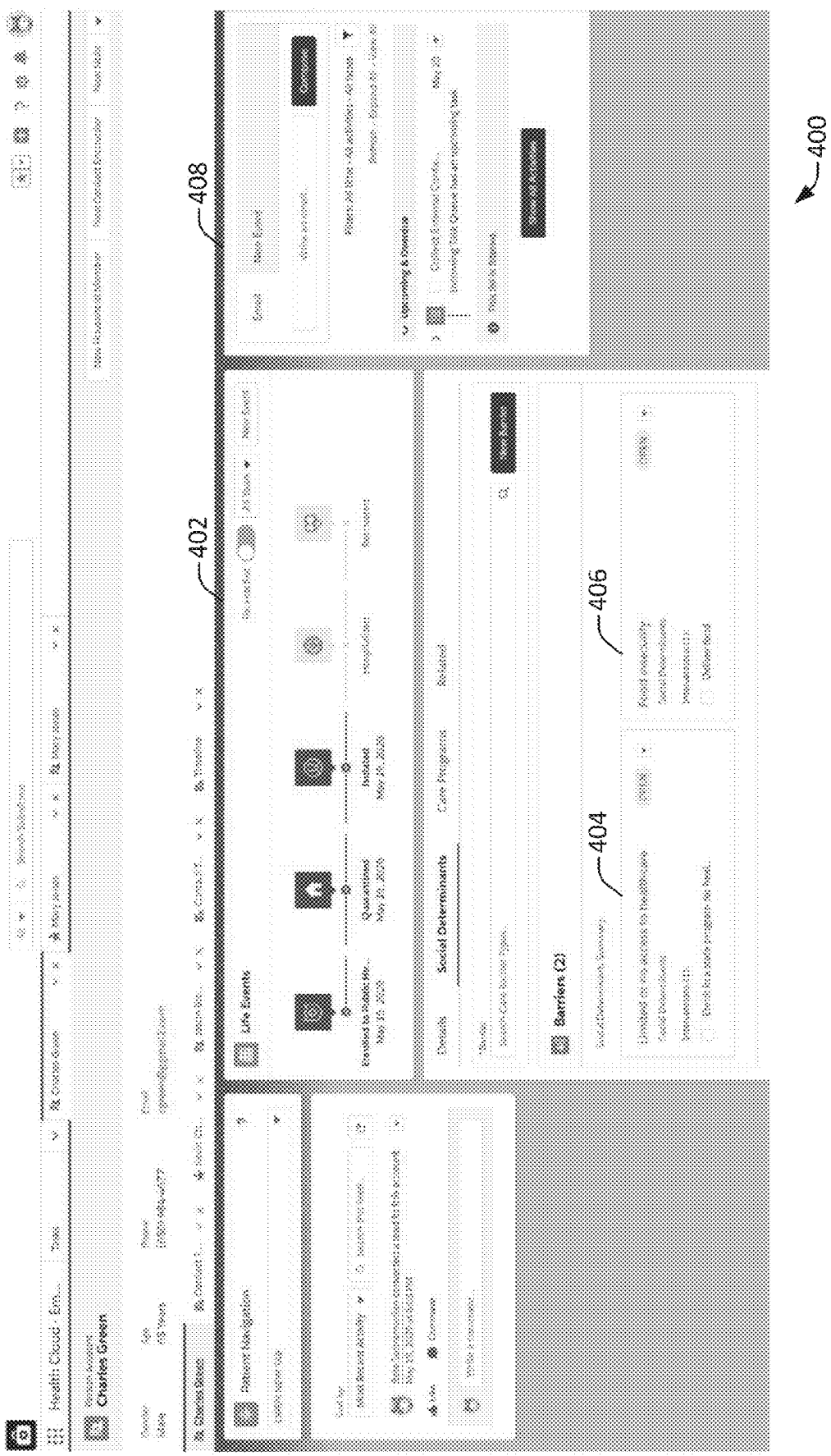
FIG. 4 illustrates an example of a user interface generated in accordance with one or more embodiments.

FIG. 4 illustrates an example of a user interface generated in accordance with one or more embodiments. In particular, FIG. 4 shows an interface 400 that displays personal information about a user. At 404, a life event timeline shows the occurrence of various events related to an illness such as Covid-19. The example person represented in the user interface 400 was added to the contact tracing system on May 15, 2020 quarantined on May 18, 2020, and isolated on May 19, 2020 but has yet to be identified as hospitalized or recovered. The example person has also been identified as being associated with two barriers to recovery, including "limited or no access to healthcare" at 404 and "food insecurity" at 406. Both barriers are associated with interventions that the contact tracer may take or recommend. In addition, the user is associated with a contact and event window at 408. The contact and event window 408 may be used to email the person or to contact the person in some other way. The contact and event window 408 may also be used to display and create events related to the person, such as collecting interaction information.

Returning to FIG. 2, an interaction for the designated person is identified at 206. According to various embodiments, an interaction may be any interaction between the designated person and another individual. An interaction may be transitory, such as a shared lunch engagement for an hour on a particular date. Alternatively, an interaction may be more permanent, such as a familial interaction in which two people live in the same household.

In some embodiments, an interaction may be determined based on a data import operation. For example, the designated person's calendar may be shared and imported to identify in-person interactions such as meetings. For at least some events, the calendar information may also be used to identify other individuals present at the event, as discussed with respect to the operation 210.

In some implementations, an interaction may be self-reported. For example, the designated individual may identify his or her family members. As another example, the designated individual may identify a meeting that included one or more people.

In some embodiments, an interaction may be determined automatically or dynamically. For example, the designated person's employment information may be used to automatically identify other individuals with whom the person likely came into contact, such as a person who shares an office with the designated person, the designated person's supervisor, the designated person's team members, and/or the designated person's subordinates. As another example, a person's identification information may be used to access information in an employee database.

One or more characteristics of the identified interaction are determined at 208. In some implementations, such characteristics may include, but are not limited to: the date and time on which the interaction was initiated, the date and time on which the interaction was concluded, and/or the type of interaction being identified. For example, the type of interaction may be classified as physical contact, as a shared meal, as a shared office space, as a shared vehicle ride, as a meeting within a conference room, as residing within the same dwelling place, or as some other type of interaction. As another example, an interaction may be characterized as a meeting in a particular conference room with six people that began at 1:15 pm on Monday, July 13 and ended at 1:45 pm on Monday, July 13.

A contact associated with the interaction is selected at 210. According to various embodiments, contacts may be selected for analysis in any of a variety of ways. For example, the designated person may identify the number and/or names of individuals associated with a particular interaction. As another example, the system may automatically identify persons associated with a particular interaction, such as the individual's family members and/or team members. As yet another example, the system may identify contacts by analyzing imported information, such as calendar events.

Personal information associated with the selected contact person is determined at 212. According to various embodiments, the personal information may include any information associated with the identification of a person. For example, a person's name, identification number, email address, phone number, social media handle, or other such information may be collected.

In some embodiments, any or all of the information described with respect to operation 208 may be collected. However, the information collected at operation 208 may include information that is available to neither the contact tracer nor the designated person. Accordingly, the personal information associated with the selected person may include contact information that may allow for more information to be collected via communication with the selected person. Additional details regarding such contact tracing operations are discussed with respect to the method 300 shown in FIG. 3.

A determination is made at 214 as to whether to select an additional contact. According to various embodiments, additional contacts may be selected until all contacts associated with the identified interaction have been processed. For example, if the identified interaction was a lunch event between four people that occurred at a particular time, and one of the four people is the designated person, then each of the other three people may be selected in turn for personal information collection.

If no additional contact is selected, then at 216 a determination is made as to whether to identify an additional interaction for the designated person. According to various embodiments, additional interactions may be selected until all interactions associated with or identified by the designated person have been analyzed.

One or more database records are created at 218 to store the collected information. According to various embodiments, the particular configuration of the database records may depend on the type of database system employed. For instance, one database record may identify personal information about the user, while each contact and each relationship associated with the user may be associated with a separate database record characterizing the contact and the relationship.

In particular embodiments, the creation of one or more database records at 218 may involve the creation of one or more tasks to orchestrate the process of contact tracing. For example, tasks may be created to identify a medical appointment, a contact tracing operation and/or an individual with whom to follow up.

According to various embodiments, the operations shown in FIG. 2 may be performed in an order different than that shown. For instance, multiple interactions may be identified at once before collecting contact information about various individuals associated with the interactions.

According to various embodiments, the operations shown in FIG. 2 may be performed asynchronously or with temporal gaps between operations. For example, a user may be enrolled in the system at one point in time, for instance via a data import operation. The user's personal information may be collected at a different point in time, for instance via an email. The user's interaction information may then be collected at a later point in time, for instance via a phone call.

In particular embodiments, information such as that collected in the method 200 shown in FIG. 2 may be imported from a third party system. For example, a geolocation system may be used to report geolocation information about individuals over time. Such information may be imported into the database via an application procedure interface (API), for example.

Figure 3:
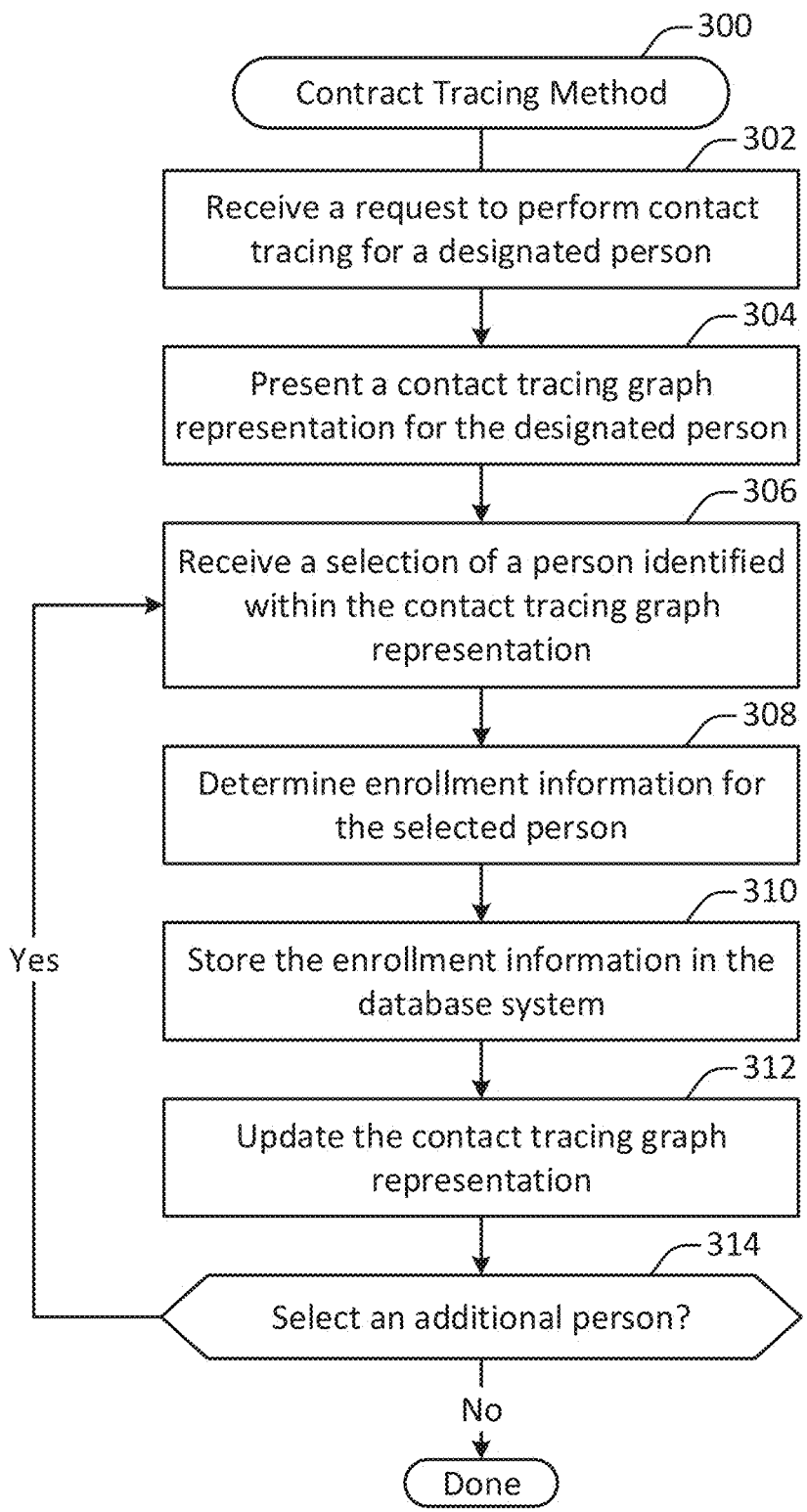
FIG. 3 illustrates an example of a method for contact tracing, performed in accordance with one or more embodiments.

FIG. 3 illustrates an example of a method 300 for contact tracing, performed in accordance with one or more embodiments. According to various embodiments the method 100 may be performed at one or more systems within an on-demand computing services environment, such as the systems and environments shown in FIGS. 9-11.

A request to perform contact tracing for a designated person is received at 302. According to various embodiments, the request may be initiated by the contact tracing system. Alternatively, or additionally, a user such as a contact tracer may initiate a request to perform contact tracing. For instance, the user may navigate to a URL associated with the contact tracing application, which may be accessed via the Internet. As part of the request to perform contact tracing, a focal individual may be selected. The focal individual's contacts may then be traced to identify and/or update information that may be relevant for public health, the focal individual's health, and/or the health of individuals with whom the focal individual may have come into contact.

A contact tracing graph representation for the designated person is presented at 304. In some implementations, a contact tracing graph representation may be presented as a collection of nodes with connections between those nodes. Alternatively, or additionally, a contact tracing graph representation may be presented in a tabular format.

Figure 5:
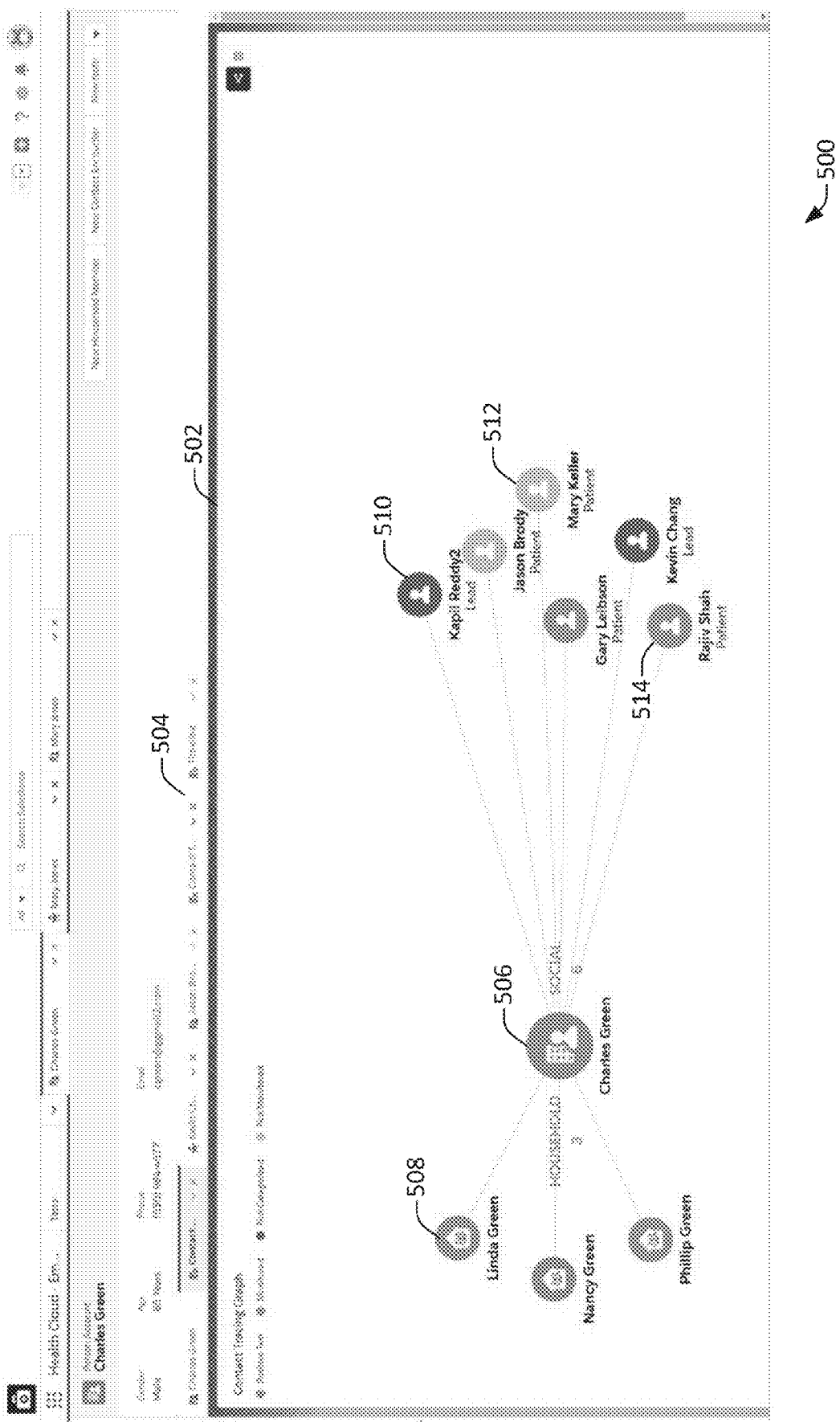
FIG. 5 illustrates an example of a user interface generated in accordance with one or more embodiments.

FIG. 5 illustrates an example of a user interface generated in accordance with one or more embodiments. In particular, FIG. 5 shows an interface 500 that displays a contact tracing graph 502. A focal person, identified as "Charles Green", is represented as a node 506. In the example shown in FIG. 5, the focal person's household contacts are shown to the left. For example, the contact "Linda Green" is represented at node 508. The focal person's professional contacts are shown on the right.

In some embodiments, colors and/or node labels may be used to provide information such as an individual's status in the system and/or infection status. For example, Kapil Reddy2 is shown in gray with a status of "Lead" at node 510 because the individual has not yet been added to the system. As another example, Mary Keller is shown in green at node 512 with a status of "Patient" because the individual has been added to the system but has not been identified as being infected. As yet another example, Rajiv Shah is shown in orange at 514 with a status of "Patient" because the individual has been added to the system and has been identified as being infected. Interactions are illustrated as lines connecting the nodes. A contact tab interface is shown at 504, identifying other user interfaces that may be used in contact tracing related to the focal individual.

Figure 6:
FIG. 6 illustrates an example of a user interface generated in accordance with one or more embodiments.

FIG. 6 illustrates an example of a user interface generated in accordance with one or more embodiments. In particular, FIG. 6 shows an interface 600 that displays a tabular representation of a contact tracing graph such as the graph shown in FIG. 5.

The focal patient's household members are shown in sub-component 602. Each individual is associated with personal information such as age, gender, testing status (e.g., Test Scheduled, Test Results Awaited, Positive Test), condition status (e.g., Symptomatic, Asymptomatic), and monitoring status (e.g., Yes No).

The focal patient's contacts that have been enrolled in the system are shown in sub-component 604. Information characterizing the encounter is also shown at 604, such as "Met friends for lunch" or "Went for basketball game."

The focal patient's contacts that have not ben enrolled in the system are shown in sub-component 606. Interaction (i.e., encounter) information is available for these leads, for instance since it was provided by the focal individual, but personal information is missing since they have not yet been enrolled.

The focal patient's encounters are shown in sub-component 608. Each encounter includes information such as the estimated participant count a start time and a location. Other information not shown in FIG. 6 may also be included, such as an interaction end time.

Returning to FIG. 3, a selection of a person identified within the contact tracing graph representation is received at 306. In some implementations, a person may be selected based on user input, for instance a mouse click within a contact tracing graph representation by a contact tracer. Alternatively, or additionally, the system may aid in selecting a person to contact.

In particular embodiments, additional individuals may be selected based at least in part on prioritization information determined by the system. For example, the system may identify particular types of interactions, such as a close and length interaction with an individual known to have tested positive for an illness, as being of particularly high priority.

Enrollment information for the selected person is determined at 308. The enrollment information is stored in the database system at 310. According to various embodiments, enrollment information for the selected person may be determined as described with respect to the method 200 shown in FIG. 2. For example, a contact tracer may email or call the selected person. As another example, the contact tracing system may send an automated notification or enrollment message to the selected person.

In particular embodiments, enrollment information may include status of enrollment and/or contact. For example, if a selected person could not be contacted, the failed enrollment attempt may be logged. As another example, if a selected person is contacted successfully but declines to be enrolled, the individual's refusal may be identified in the system. For instance, a selected person who declines to be enrolled may still be later informed of relevant contact tracing information.

The contact tracing graph representation is updated at 312. According to various embodiments, the contact tracing graph representation may be updated to reflect the enrollment information determined and stored at operations 308 and 310. For example, individuals may be added to or removed from the contact tracing graph representation. As another example, the enrollment status, medical status, personal identification information, or other such data associated with an individual may be changed. Such changes may be reflected as changes to labels, changes to node colors, changes to edges connecting nodes, or changes to any other user interface sub-component within the contact tracing graph representation related to the focal person.

A determination is made as to whether to select an additional person at 314. In some implementations, a user such as a contact tracer may make the determination, for instance by deciding whether to click on another node within the contact tracing graph representation. Alternatively, the system may select additional persons based on contact tracing information. For example, additional persons may continue to be selected so long as there are persons who have interacted with the selected person and have not yet been contacted. As another example, additional persons may be selected at random or based on one or more system-defined selection criteria. For instance, if an individual has been in contact with many other people, the system may select only some of those people if the individual has not tested positive for an illness and is not symptomatic.

Figure 7:
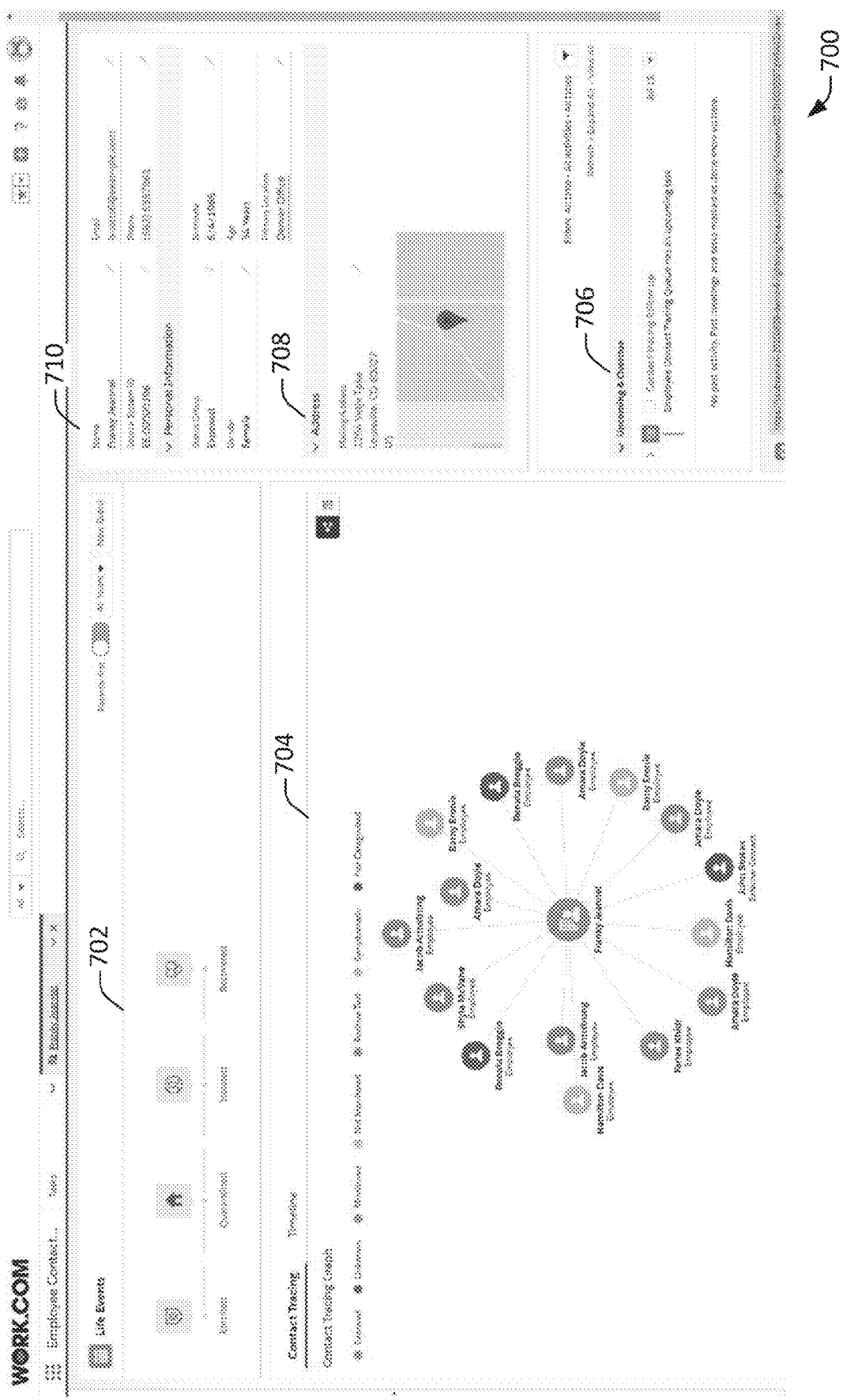
FIG. 7 illustrates an example of a user interface generated in accordance with one or more embodiments.

FIG. 7 illustrates an example of a user interface generated in accordance with one or more embodiments. In particular, FIG. 7 shows an interface 700 that displays multiple sub-components of information about a focal user. These sub-components include a life event timeline sub-component 702, a contact tracing graph sub-component 704, an event information sub-component 706, an address sub-component 708, and an personal information sub-component 710.

Figure 8:
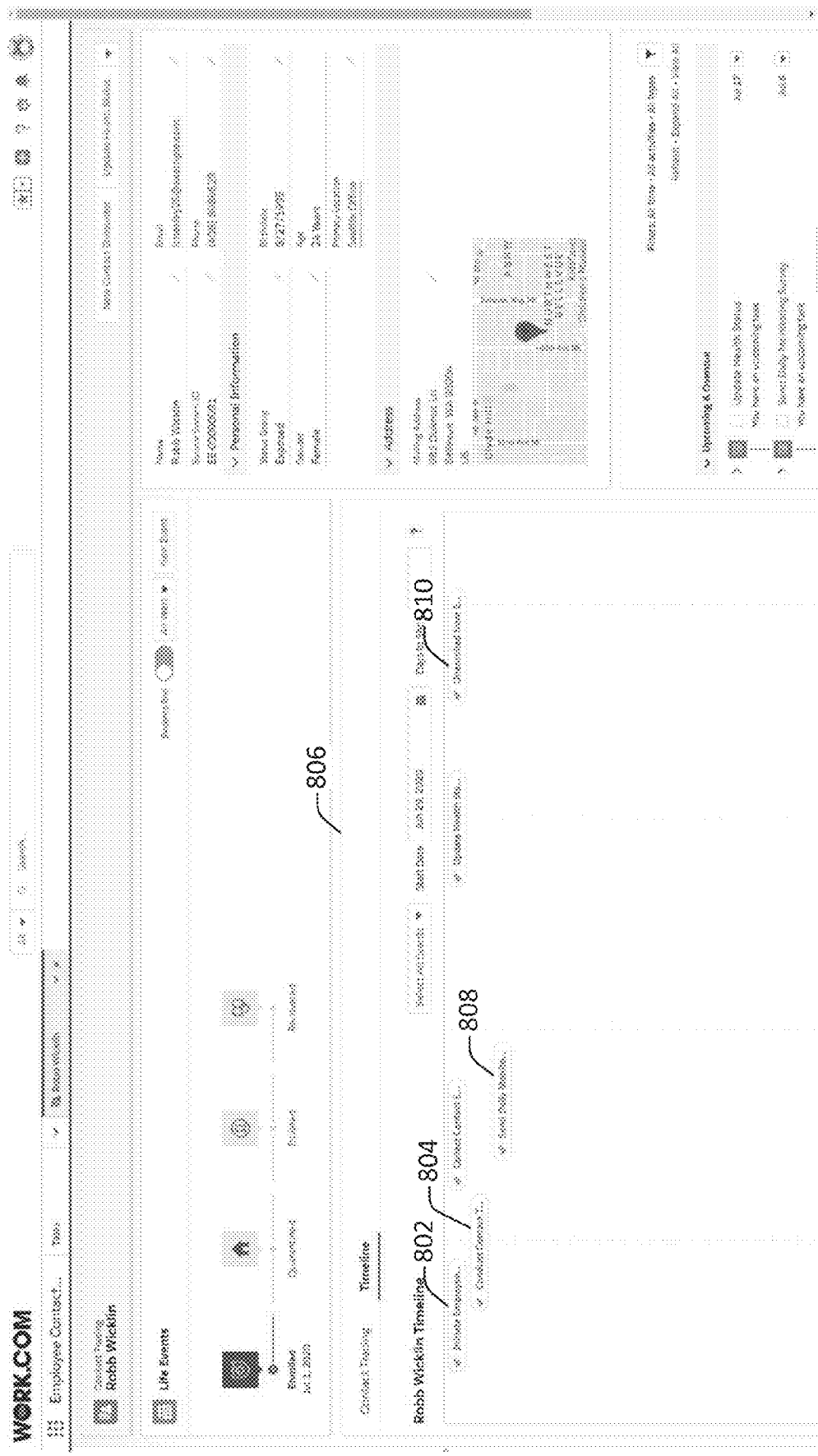
FIG. 8 illustrates an example of a user interface generated in accordance with one or more embodiments.

FIG. 8 illustrates an example of a user interface generated in accordance with one or more embodiments. In particular, FIG. 8 shows an interface 800 that displays multiple sub-components of information about a focal user. The interface 800 is substantially similar the interface 700 shown in 700, with the exception that a timeline 806 is shown instead of a contact tracing graph. The timeline 806 illustrates events associated with an individual displayed on a timeline. For example, events are shown that correspond to the enrollment of the individual at 802, the initial contact tracing interview at 804, a daily monitoring task at 808, and unenrollment at 810.

Figure 12:
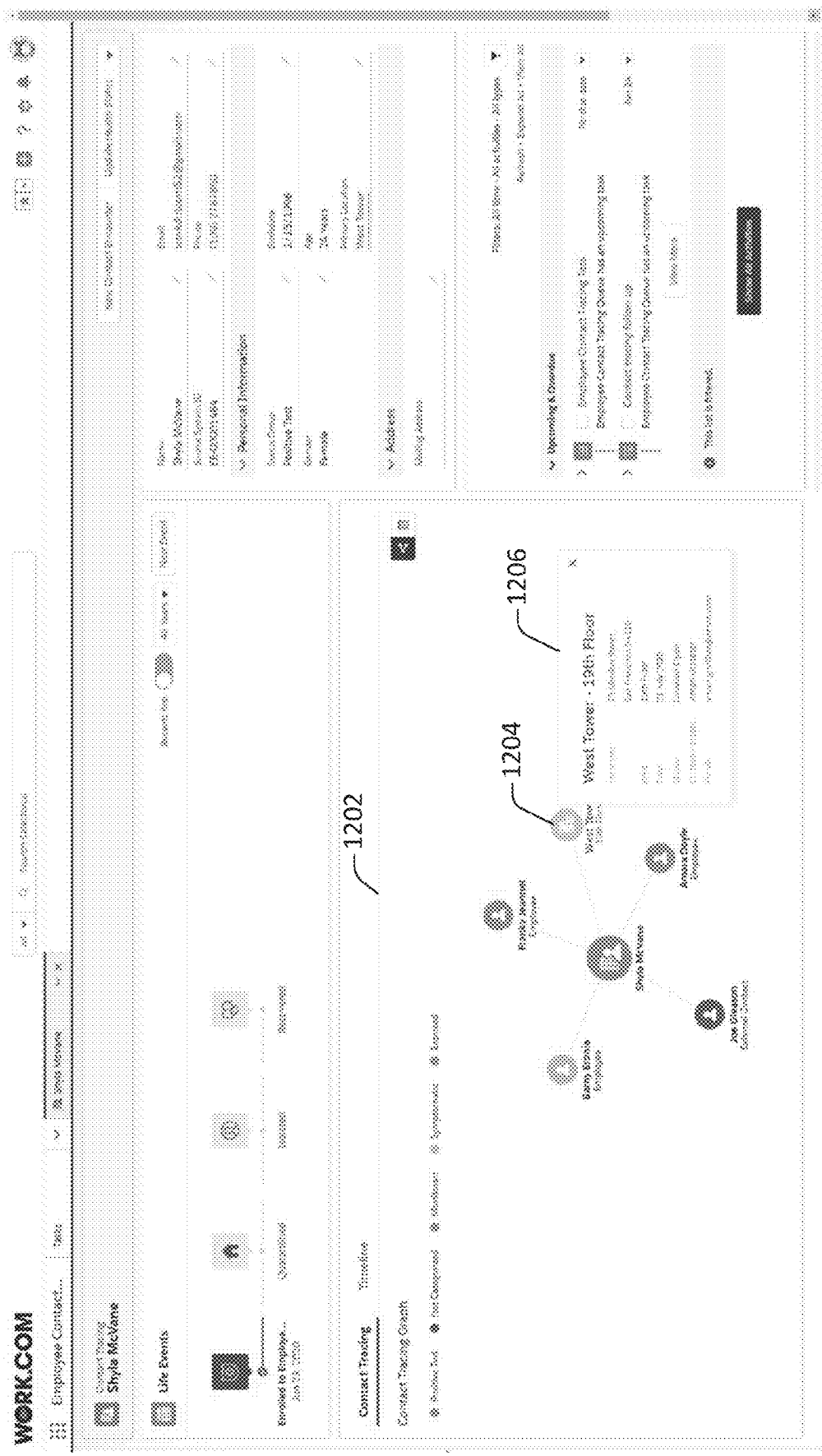
FIG. 12 illustrates an example of a user interface generated in accordance with one or more embodiments.

FIG. 12 illustrates an example of a user interface generated in accordance with one or more embodiments. In FIG. 12, a contact tracing graph 1202 is shown. The contact tracing graph 1202 includes a node 1204 that corresponds to a floor of a building. In this way, the contact tracing graph may be used to represent more attenuated connections than direct physical interaction, such as sharing a physical space in a work environment. According to various embodiments, a node in a graph may correspond with a private physical location, a public physical location, an indeterminate event, or any suitable unit of analysis.

Figure 13:
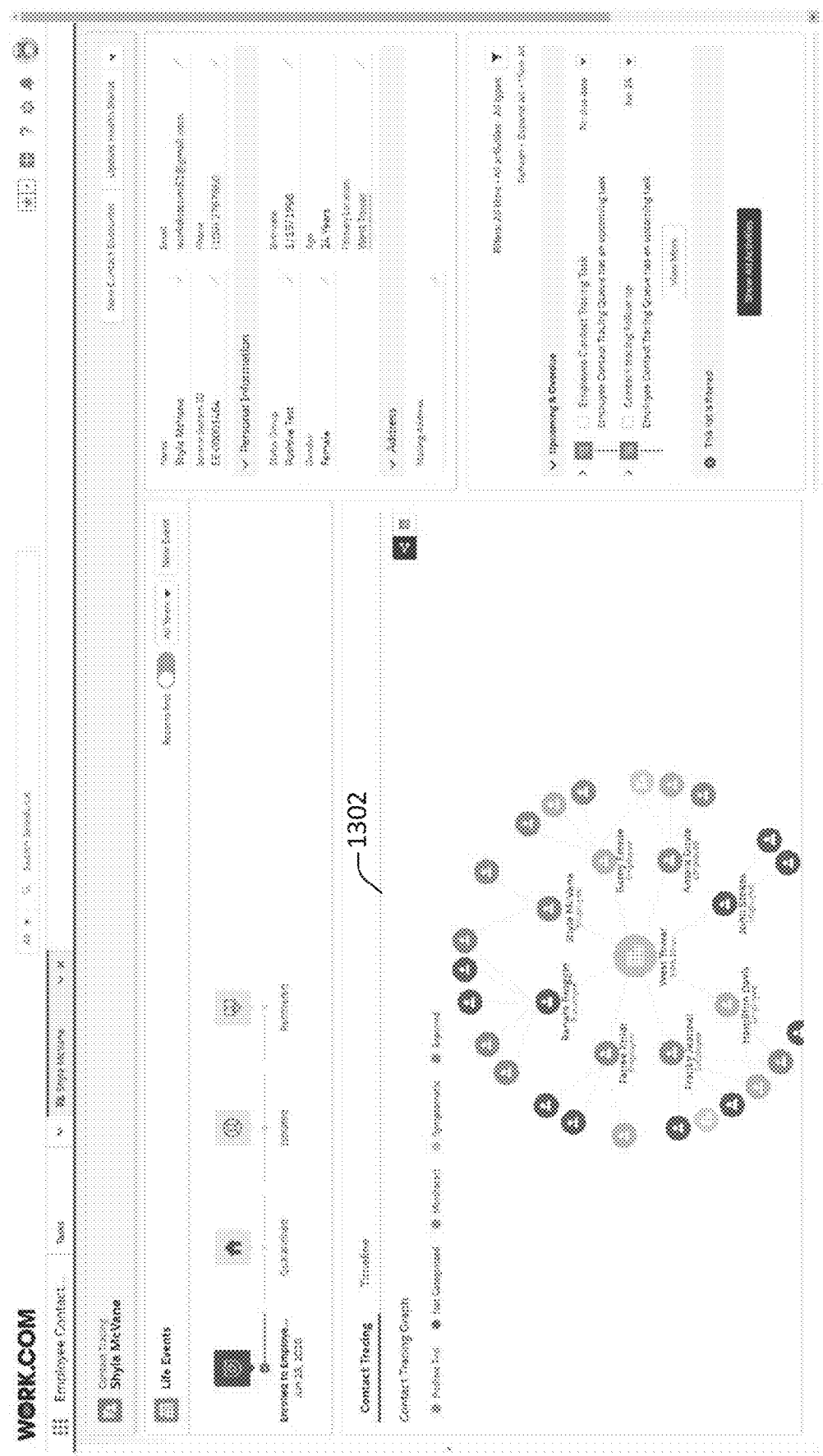
FIG. 13 illustrates an example of a user interface generated in accordance with one or more embodiments.

FIG. 13 illustrates an example of a user interface generated in accordance with one or more embodiments. After selecting the node 1204 in FIG. 12, the individuals who work on the floor may be shown in a contact tracing graph at 1302.

Figure 14:
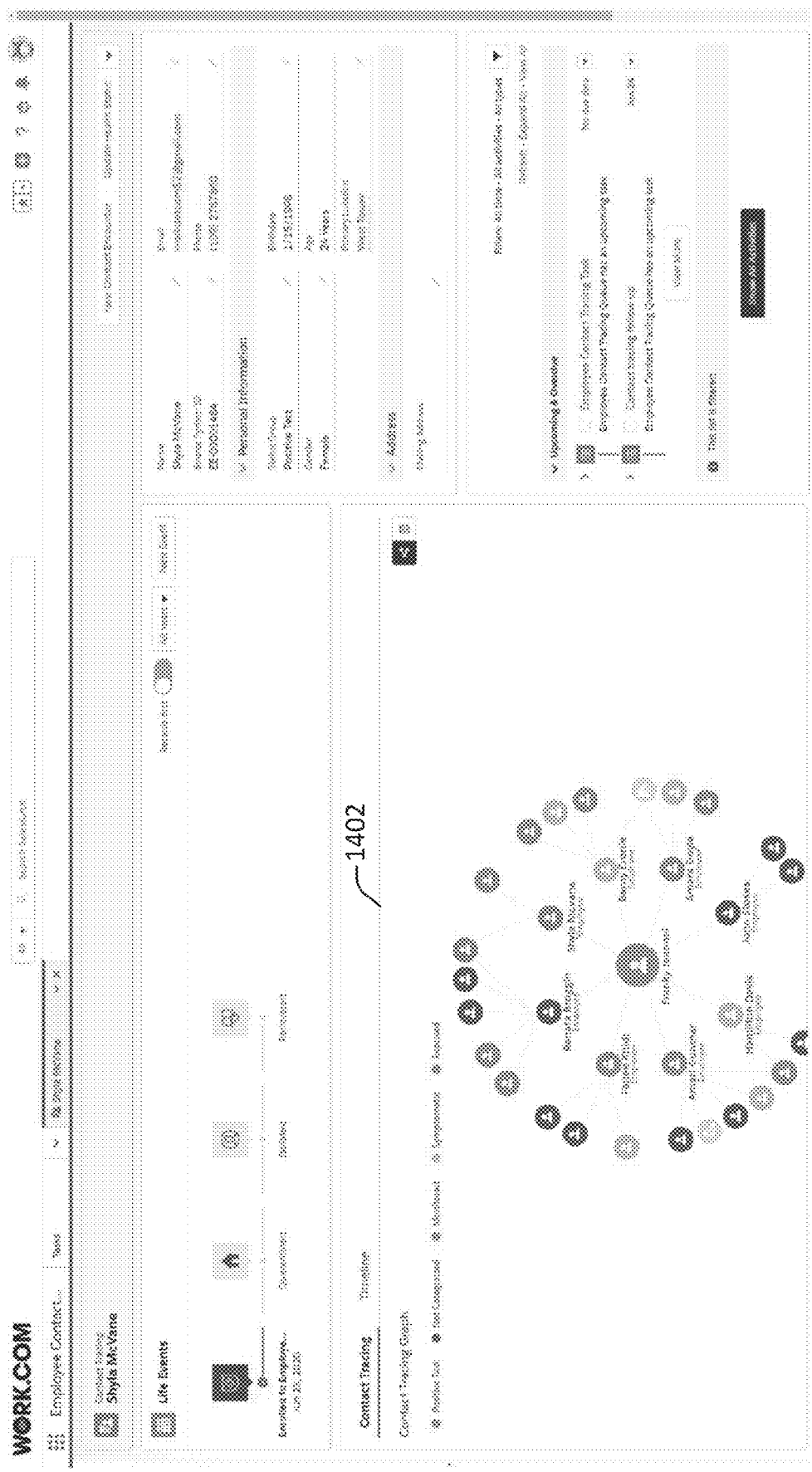
FIG. 14 illustrates an example of a user interface generated in accordance with one or more embodiments.

FIG. 14 illustrates an example of a user interface generated in accordance with one or more embodiments. In FIG. 14, in contrast to FIG. 7, two degrees of connection from the focal individual are presented. According to various embodiments, the number of degrees of connection from a focal node may be user-configurable. Alternatively, or additionally, the system may select an appropriate number of degrees of separation in order to present the contact tracing graph representation.

Figure 15:
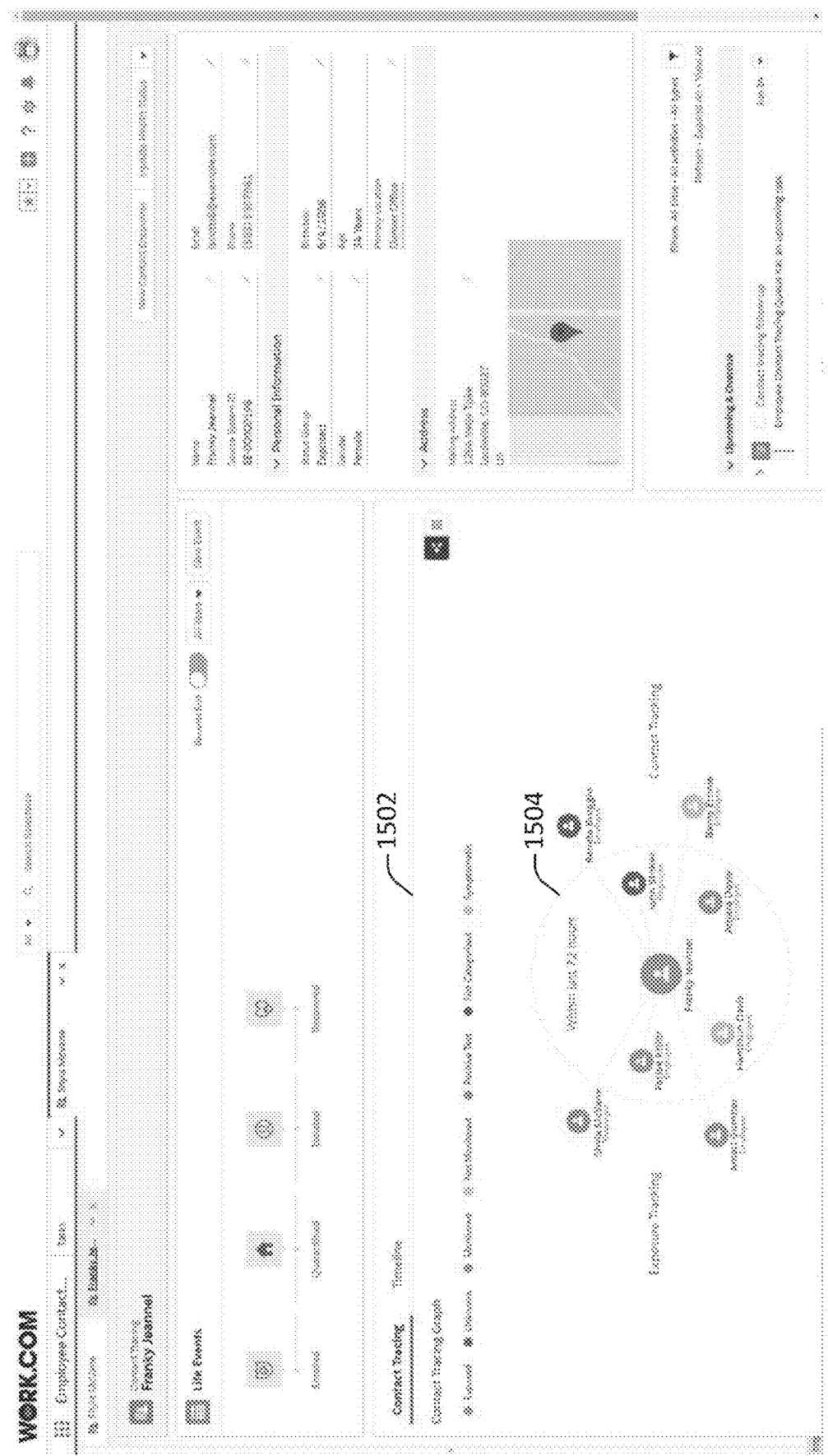
FIG. 15 illustrates an example of a user interface generated in accordance with one or more embodiments.

FIG. 15 illustrates an example of a user interface generated in accordance with one or more embodiments. In FIG. 15, the contact tracing graph 1502 includes a barrier 1504 that identifies contacts with whom the focal individual interacted within the last 72 hours. In this way, the contact tracing graph may be used to perform both contact tracing and exposure tracing on a single graph. That is, the contact tracing graph may be used both to identify people who may have been exposed to a disease by a designated individual and to identify people to whom the designated individual had been exposed prior to being infected with the disease.

Figure 9:
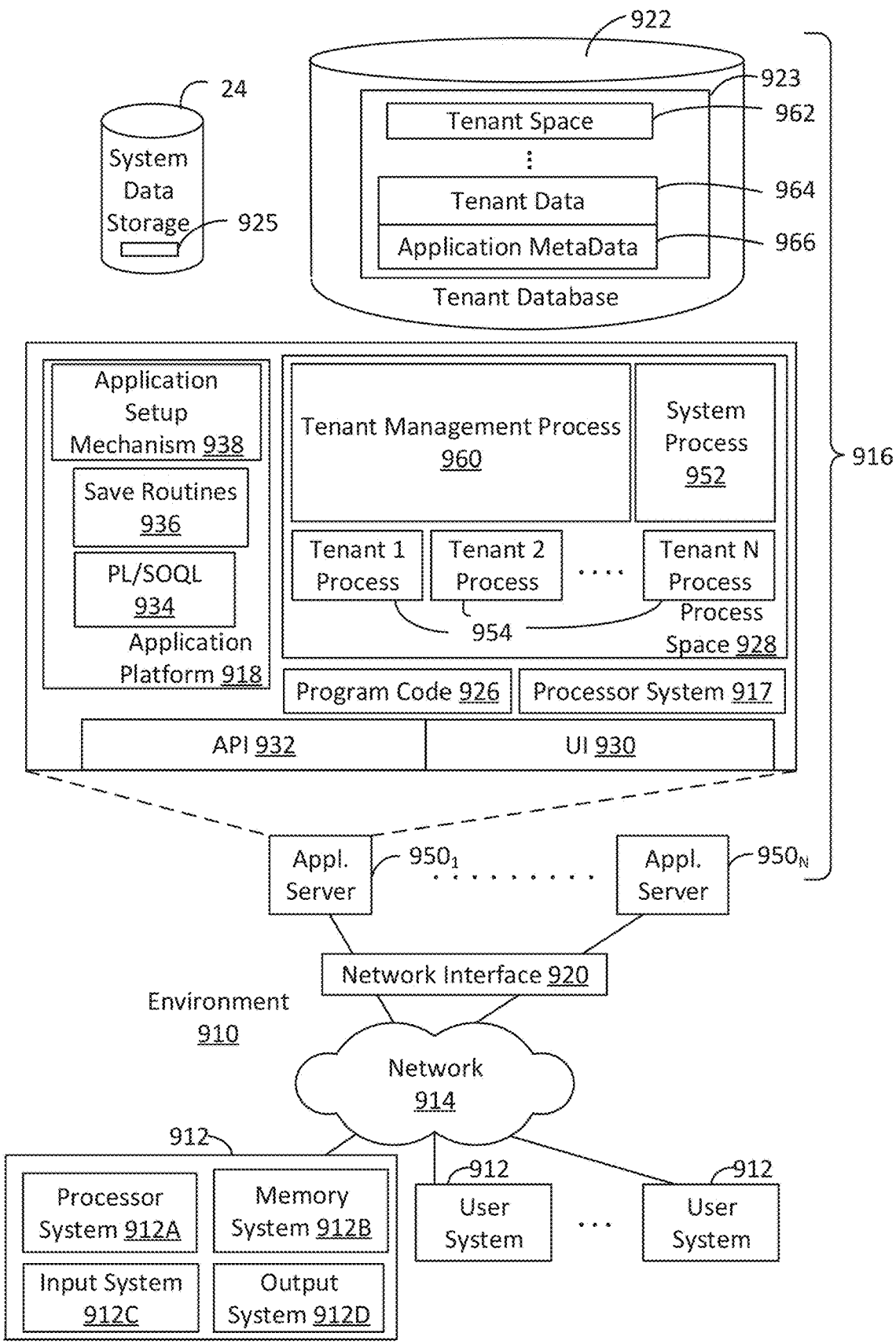
FIG. 9 shows a block diagram of an example of an environment that includes an on-demand database service configured in accordance with some implementations.

FIG. 9 shows a block diagram of an example of an environment 910 that includes an on-demand database service configured in accordance with some implementations. Environment 910 may include user systems 912, network 914, database system 916, processor system 917, application platform 918, network interface 920, tenant data storage 922, tenant data 923, system data storage 924, system data 925, program code 926, process space 928, User Interface (UI) 930, Application Program Interface (API) 932, PL/SOQL 934, save routines 936, application setup mechanism 938, application servers 950-1 through 950-N, system process space 952, tenant process spaces 954, tenant management process space 960, tenant storage space 962, user storage 964, and application metadata 966. Some of such devices may be implemented using hardware or a combination of hardware and software and may be implemented on the same physical device or on different devices. Thus, terms such as "data processing apparatus," "machine," "server" and "device" as used herein are not limited to a single hardware device, but rather include any hardware and software configured to provide the described functionality.

An on-demand database service, implemented using system 916 may be managed by a database service provider. Some services may store information from one or more tenants into tables of a common database image to form a multi-tenant database system (MTS). As used herein, each MIS could include one or more logically and/or physically connected servers distributed locally or across one or more geographic locations. Databases described herein may be implemented as single databases, distributed databases, collections of distributed databases, or any other suitable database system. A database image may include one or more database objects. A relational database management system (RDBMS) or a similar system may execute storage and retrieval of information against these objects.

In some implementations, the application platform 918 may be a framework that allows the creation, management, and execution of applications in system 916. Such applications may be developed by the database service provider or by users or third-party application developers accessing the service. Application platform 918 includes an application setup mechanism 938 that supports application developers' creation and management of applications, which may be saved as metadata into tenant data storage 922 by save routines 936 for execution by subscribers as one or more tenant process spaces 954 managed by tenant management process 960 for example. Invocations to such applications may be coded using PL/SOQL 934 that provides a programming language style interface extension to API 932. A detailed description of some PL/SOQL language implementations is discussed in commonly assigned U.S. Pat. No. 7,730,478, titled METHOD AND SYSTEM FOR ALLOWING ACCESS TO DEVELOPED APPLICATIONS VIA A MULTI-TENANT ON-DEMAND DATABASE SERVICE, by Craig Weissman, issued on Jun. 1, 2010, and hereby incorporated by reference in its entirety and for all purposes. Invocations to applications may be detected by one or more system processes. Such system processes may manage retrieval of application metadata 966 for a subscriber making such an invocation. Such system processes may also manage execution of application metadata 966 as an application in a virtual machine.

In some implementations, each application server 950 may handle requests for any user associated with any organization. A load balancing function (e.g., an F5 Big-IP load balancer) may distribute requests to the application servers 950 based on an algorithm such as least-connections, round robin, observed response time, etc. Each application server 950 may be configured to communicate with tenant data storage 922 and the tenant data 923 therein, and system data storage 924 and the system data 925 therein to serve requests of user systems 912. The tenant data 923 may be divided into individual tenant storage spaces 962 which can be either a physical arrangement and/or a logical arrangement of data. Within each tenant storage space 962, user storage 964 and application metadata 966 may be similarly allocated for each user. For example, a copy of a user's most recently used (MRU) items might be stored to user storage 964. Similarly, a copy of MRU items for an entire tenant organization may be stored to tenant storage space 962. A UI 930 provides a user interface and an API 932 provides an application programming interface to system 916 resident processes to users and/or developers at user systems 912.

System 916 may implement a web-based contact tracing system. For example, in some implementations, system 916 may include application servers configured to implement and execute contact tracing software applications. The application servers may be configured to provide related data, code, forms, web pages and other information to and from user systems 912. Additionally, the application servers may be configured to store information to, and retrieve information from a database system. Such information may include related data, objects, and/or Webpage content. With a multi-tenant system, data for multiple tenants may be stored in the same physical database object in tenant data storage 922, however, tenant data may be arranged in the storage medium(s) of tenant data storage 922 so that data of one tenant is kept logically separate from that of other tenants. In such a scheme, one tenant may not access another tenant's data, unless such data is expressly shared.

Several elements in the system shown in FIG. 9 include conventional, well-known elements that are explained only briefly here. For example, user system 912 may include processor system 912A, memory system 912B, input system 912C, and output system 912D. A user system 912 may be implemented as any computing device(s) or other data processing apparatus such as a mobile phone, laptop computer, tablet, desktop computer, or network of computing devices. User system 12 may run an internet browser allowing a user (e.g., a subscriber of an MTS) of user system 912 to access, process and view information, pages and applications available from system 916 over network 914. Network 914 may be any network or combination of networks of devices that communicate with one another, such as any one or any combination of a LAN (local area network), WAN (wide area network), wireless network, or other appropriate configuration.

The users of user systems 912 may differ in their respective capacities, and the capacity of a particular user system 912 to access information may be determined at least in part by "permissions" of the particular user system 912. As discussed herein, permissions generally govern access to computing resources such as data objects, components, and other entities of a computing system, such as a contact tracing system, a healthcare system, a social networking system, and/or a CRM database system. "Permission sets" generally refer to groups of permissions that may be assigned to users of such a computing environment. For instance, the assignments of users and permission sets may be stored in one or more databases of System 916. Thus, users may receive permission to access certain resources. A permission server in an on-demand database service environment can store criteria data regarding the types of users and permission sets to assign to each other. For example a computing device can provide to the server data indicating an attribute of a user (e.g., geographic location, industry, role, level of experience, etc.) and particular permissions to be assigned to the users fitting the attributes. Permission sets meeting the criteria may be selected and assigned to the users. Moreover, permissions may appear in multiple permission sets. In this way, the users can gain access to the components of a system.

In some an on-demand database service environments, an Application Programming Interface (API) may be configured to expose a collection of permissions and their assignments to users through appropriate network-based services and architectures, for instance, using Simple Object Access Protocol (SOAP) Web Service and Representational State Transfer (REST) APIs.

In some implementations, a permission set may be presented to an administrator as a container of permissions. However, each permission in such a permission set may reside in a separate API object exposed in a shared API that has a child-parent interaction with the same permission set object. This allows a given permission set to scale to millions of permissions for a user while allowing a developer to take advantage of joins across the API objects to query, insert, update, and delete any permission across the millions of possible choices. This makes the API highly scalable, reliable, and efficient for developers to use.

In some implementations, a permission set API constructed using the techniques disclosed herein can provide scalable, reliable, and efficient mechanisms for a developer to create tools that manage a user's permissions across various sets of access controls and across types of users. Administrators who use this tooling can effectively reduce their time managing a user's rights, integrate with external systems, and report on rights for auditing and troubleshooting purposes. By way of example, different users may have different capabilities with regard to accessing and modifying application and database information, depending on a user's security or permission level, also called authorization. In systems with a hierarchical role model, users at one permission level may have access to applications, data, and database information accessible by a lower permission level user, but may not have access to certain applications, database information, and data accessible by a user at a higher permission level.

As discussed above, system 916 may provide on-demand database service to user systems 912 using an MIS arrangement. By way of example, one tenant organization may be a company that employs a sales force where each salesperson uses system 916 to manage their sales process. Thus, a user in such an organization may maintain contact data, leads data, customer follow-up data, performance data, goals and progress data, etc., all applicable to that user's personal sales process (e.g., in tenant data storage 922). In this arrangement, a user may manage his or her sales efforts and cycles from a variety of devices, since relevant data and applications to interact with (e.g., access, view, modify, report, transmit, calculate, etc.) such data may be maintained and accessed by any user system 912 having network access.

When implemented in an MTS arrangement, system 916 may separate and share data between users and at the organization-level in a variety of manners. For example, for certain types of data each user's data might be separate from other users' data regardless of the organization employing such users. Other data may be organization-wide data, which is shared or accessible by several users or potentially all users form a given tenant organization. Thus, some data structures managed by system 916 may be allocated at the tenant level while other data structures might be managed at the user level. Because an MTS might support multiple tenants including possible competitors, the MTS may have security protocols that keep data, applications, and application use separate. In addition to user-specific data and tenant-specific data, system 916 may also maintain system-level data usable by multiple tenants or other data. Such system-level data may include industry reports, news, postings, and the like that are sharable between tenant organizations.

In some implementations, user systems 912 may be client systems communicating with application servers 950 to request and update system-level and tenant-level data from system 916. By way of example, user systems 912 may send one or more queries requesting data of a database maintained in tenant data storage 922 and/or system data storage 924. An application server 950 of system 916 may automatically generate one or more SQL statements (e.g., one or more SQL queries) that are designed to access the requested data. System data storage 924 may generate query plans to access the requested data from the database.

The database systems described herein may be used for a variety of database applications. By way of example, each database can generally be viewed as a collection of objects, such as a set of logical tables, containing data fitted into predefined categories. A "table" is one representation of a data object, and may be used herein to simplify the conceptual description of objects and custom objects according to some implementations. It should be understood that "table" and "object" may be used interchangeably herein. Each table generally contains one or more data categories logically arranged as columns or fields in a viewable schema. Each row or record of a table contains an instance of data for each category defined by the fields. For example, a CRM database may include a table that describes a customer with fields for basic contact information such as name, address, phone number, fax number, etc. Another table might describe a purchase order, including fields for information such as customer, product, sale price, date, etc. In some multi-tenant database systems, standard entity tables might be provided for use by all tenants. For contact tracing applications, each organization may be associated with a distinct set of user records and linkages between user records. For CRM database applications, such standard entities might include tables for case, account, contact, lead, and opportunity data objects, each containing pre-defined fields. It should be understood that the word "entity" may also be used interchangeably herein with "object" and "table".

In some implementations, tenants may be allowed to create and store custom objects, or they may be allowed to customize standard entities or objects, for example by creating custom fields for standard objects, including custom index fields. Commonly assigned U.S. Pat. No. 7,779,039, titled CUSTOM ENTITIES AND FIELDS IN A MULTI-TENANT DATABASE SYSTEM, by Weissman et al., issued on Aug. 17, 2010, and hereby incorporated by reference in its entirety and for all purposes, teaches systems and methods for creating custom objects as well as customizing standard objects in an MTS. In certain implementations, for example, all custom entity data rows may be stored in a single multi-tenant physical table, which may contain multiple logical tables per organization. It may be transparent to customers that their multiple "tables" are in fact stored in one large table or that their data may be stored in the same table as the data of other customers.

Figure 10A:
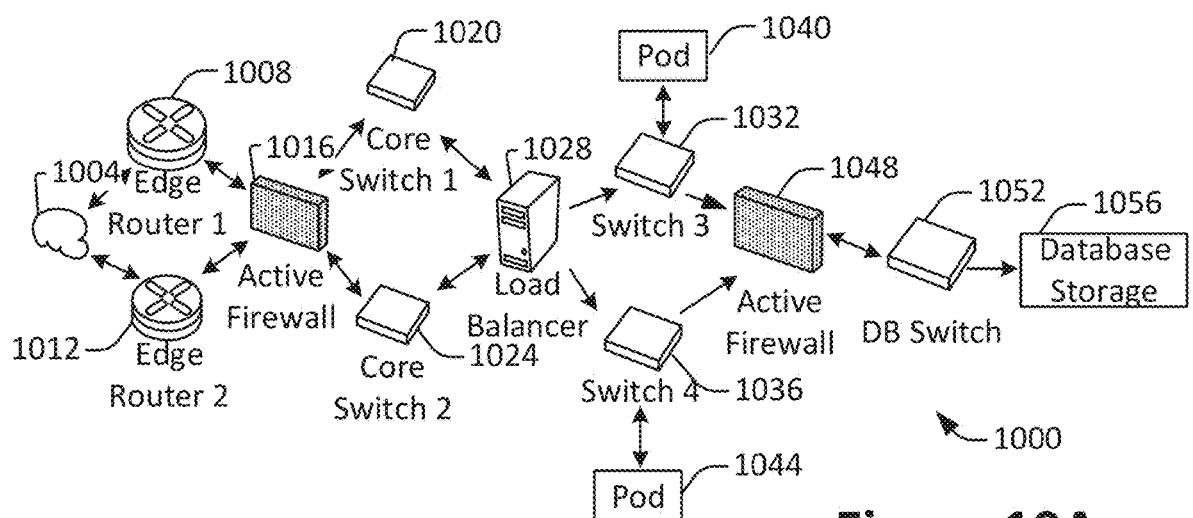
FIG. 10A shows a system diagram of an example of architectural components of an on-demand database service environment, configured in accordance with some implementations.

FIG. 10A shows a system diagram of an example of architectural components of an on-demand database service environment 1000, configured in accordance with some implementations. A client machine located in the cloud 1004 may communicate with the on-demand database service environment via one or more edge routers 1008 and 1012. A client machine may include any of the examples of user systems ?12 described above. The edge routers 1008 and 1012 may communicate with one or more core switches 1020 and 1024 via firewall 1016. The core switches may communicate with a load balancer 1028 which may distribute server load over different pods, such as the pods 1040 and 1044 by communication via pod switches 1032 and 1036. The pods 1040 and 1044, which may each include one or more servers and/or other computing resources, may perform data processing and other operations used to provide on-demand services. Components of the environment may communicate with a database storage 1056 via a database firewall 1048 and a database switch 1052.

Accessing an on-demand database service environment may involve communications transmitted among a variety of different components. The environment 1000 is a simplified representation of an actual on-demand database service environment. For example some implementations of an on-demand database service environment may include anywhere from one to many devices of each type. Additionally, an on-demand database service environment need not include each device shown, or may include additional devices not shown, in FIGS. 10A and 10B.

The cloud 1004 refers to any suitable data network or combination of data networks, which may include the Internet. Client machines located in the cloud 1004 may communicate with the on-demand database service environment 1000 to access services provided by the on-demand database service environment 1000. By way of example, client machines may access the on-demand database service environment 1000 to retrieve, store, edit, and/or process contact tracing information.

In some implementations, the edge routers 1008 and 1012 route packets between the cloud 1004 and other components of the on-demand database service environment 1000. The edge routers 1008 and 1012 may employ the Border Gateway Protocol (BGP). The edge routers 1008 and 1012 may maintain a table of IP networks or 'prefixes', which designate network reachability among autonomous systems on the internet.

In one or more implementations, the firewall 1016 may protect the inner components of the environment 1000 from internet traffic. The firewall 1016 may block, permit, or deny access to the inner components of the on-demand database service environment 1000 based upon a set of rules and/or other criteria. The firewall 1016 may act as one or more of a packet filter, an application gateway, a stateful filter, a proxy server, or any other type of firewall.

In some implementations the core switches 1020 and 1024 may be high-capacity switches that transfer packets within the environment 1000. The core switches 1020 and 1024 may be configured as network bridges that quickly route data between different components within the on-demand database service environment. The use of two or more core switches 1020 and 1024 may provide redundancy and/or reduced latency.

In some implementations, communication between the pods 1040 and 1044 may be conducted via the pod switches 1032 and 1036. The pod switches 1032 and 1036 may facilitate communication between the pods 1040 and 1044 and client machines, for example via core switches 1020 and 1024. Also or alternatively, the pod switches 1032 and 1036 may facilitate communication between the pods 1040 and 1044 and the database storage 1056. The load balancer 1028 may distribute workload between the pods, which may assist in improving the use of resources, increasing throughput, reducing response times, and/or reducing overhead. The load balancer 1028 may include multilayer switches to analyze and forward traffic.

In some implementations, access to the database storage 1056 may be guarded by a database firewall 1048, which may act as a computer application firewall operating at the database application layer of a protocol stack. The database firewall 1048 may protect the database storage 1056 from application attacks such as structure query language (SQL) injection, database rootkits, and unauthorized information disclosure. The database firewall 1048 may include a host using one or more forms of reverse proxy services to proxy traffic before passing it to a gateway router and/or may inspect the contents of database traffic and block certain content or database requests. The database firewall 1048 may work on the SQL application level atop the TCP/IP stack, managing applications' connection to the database or SQL management interfaces as well as intercepting and enforcing packets traveling to or from a database network or application interface.

In some implementations, the database storage 1056 may be an on-demand database system shared by many different organizations. The on-demand database service may employ a single-tenant approach, a multi-tenant approach, a virtualized approach, or any other type of database approach. Communication with the database storage 1056 may be conducted via the database switch 1052. The database storage 1056 may include various software components for handling database queries. Accordingly, the database switch 1052 may direct database queries transmitted by other components of the environment (e.g., the pods 1040 and 1044) to the correct components within the database storage 1056.

Figure 10B:
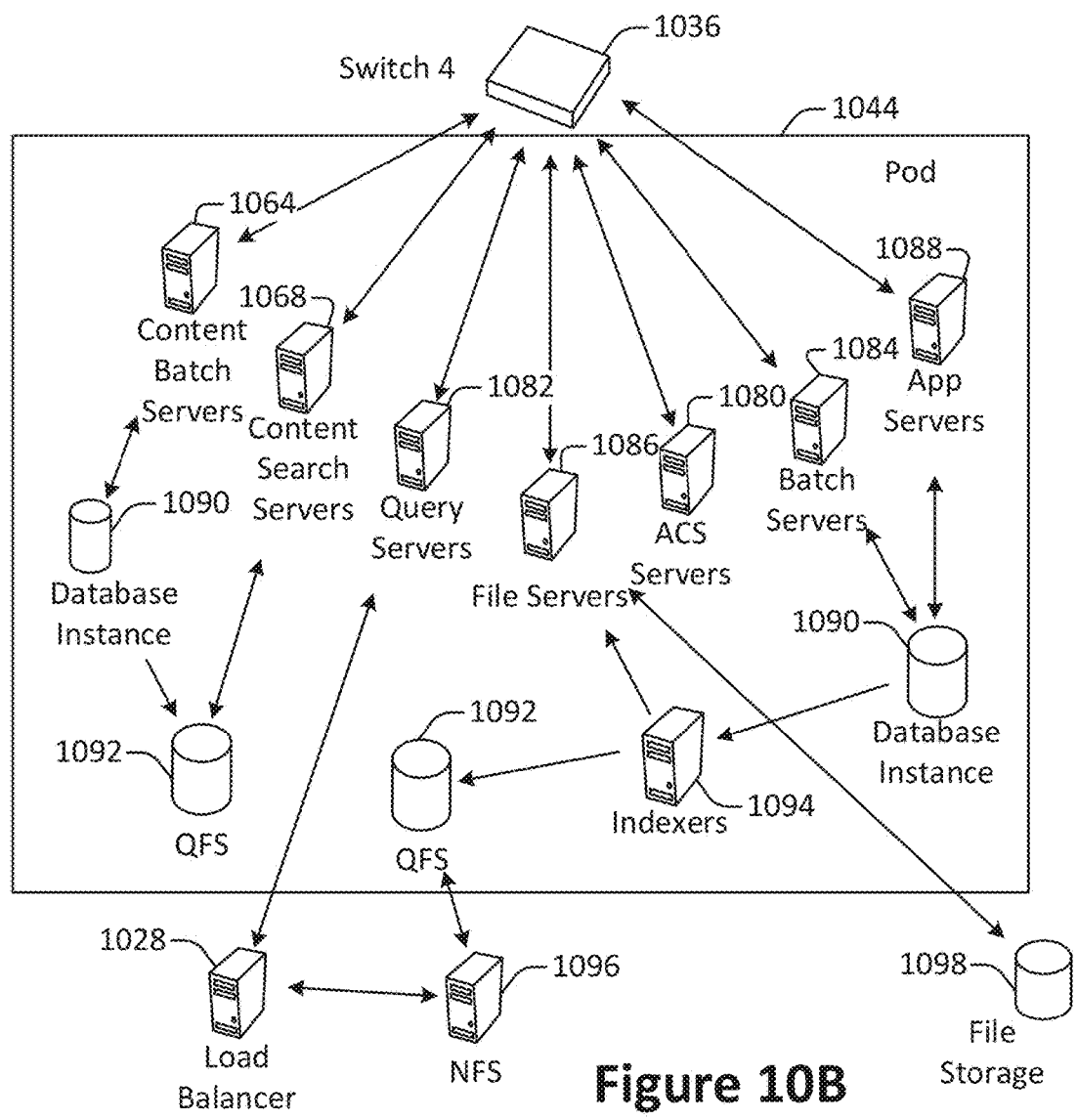
FIG. 10B shows a system diagram further illustrating an example of architectural components of an on-demand database service environment, in accordance with some implementations.

FIG. 10B shows a system diagram further illustrating an example of architectural components of an on-demand database service environment, in accordance with some implementations. The pod 1044 may be used to render services to user(s) of the on-demand database service environment 1000. The pod 1044 may include one or more content batch servers 1064, content search servers 1068, query servers 1082, file servers 1086, access control system (ACS) servers 1080, batch servers 1084, and app servers 1088. Also, the pod 1044 may include database instances 1090, quick file systems (QFS) 1092, and indexers 1094. Some or all communication between the servers in the pod 1044 may be transmitted via the switch 1036.

In some implementations, the app servers 1088 may include a framework dedicated to the execution of procedures (e.g., programs, routines, scripts) for supporting the construction of applications provided by the on-demand database service environment 1000 via the pod 1044. One or more instances of the app server 1088 may be configured to execute all or a portion of the operations of the services described herein.

In some implementations, as discussed above, the pod 1044 may include one or more database instances 1090. A database instance 1090 may be configured as an MTS in which different organizations share access to the same database, using the techniques described above. Database information may be transmitted to the indexer 1094, which may provide an index of information available in the database 1090 to file servers 1086. The QFS 1092 or other suitable filesystem may serve as a rapid-access file system for storing and accessing information available within the pod 1044. The QFS 1092 may support volume management capabilities, allowing many disks to be grouped together into a file system. The QFS 1092 may communicate with the database instances 1090, content search servers 1068 and/or indexers 1094 to identify, retrieve, move, and/or update data stored in the network file systems (NFS) 1096 and/or other storage systems.

In some implementations, one or more query servers 1082 may communicate with the NFS 1096 to retrieve and/or update information stored outside of the pod 1044. The NFS 1096 may allow servers located in the pod 1044 to access information over a network in a manner similar to how local storage is accessed. Queries from the query servers 1022 may be transmitted to the NFS 1096 via the load balancer 1028, which may distribute resource requests over various resources available in the on-demand database service environment 1000. The NFS 1096 may also communicate with the QFS 1092 to update the information stored on the NFS 1096 and/or to provide information to the QFS 1092 for use by servers located within the pod 1044.

In some implementations, the content batch servers 1064 may handle requests internal to the pod 1044. These requests may be long-running and/or not tied to a particular customer, such as requests related to log mining, cleanup work, and maintenance tasks. The content search servers 1068 may provide query and indexer functions such as functions allowing users to search through content stored in the on-demand database service environment 1000. The file servers 1086 may manage requests for information stored in the file storage 1098, which may store information such as documents, images, basic large objects (BLOBs), etc. The query servers 1082 may be used to retrieve information from one or more file systems. For example, the query system 1082 may receive requests for information from the app servers 1088 and then transmit information queries to the NFS 1096 located outside the pod 1044. The ACS servers 1080 may control access to data, hardware resources, or software resources called upon to render services provided by the pod 1044. The batch servers 1084 may process batch jobs, which are used to run tasks at specified times. Thus, the batch servers 1084 may transmit instructions to other servers, such as the app servers 1088, to trigger the batch jobs.

While some of the disclosed implementations may be described with reference to a system having an application server providing a front end for an on-demand database service capable of supporting multiple tenants, the disclosed implementations are not limited to multi-tenant databases nor deployment on application servers. Some implementations may be practiced using various database architectures such as ORACLE®, DB2® by IBM and the like without departing from the scope of present disclosure.

Figure 11:
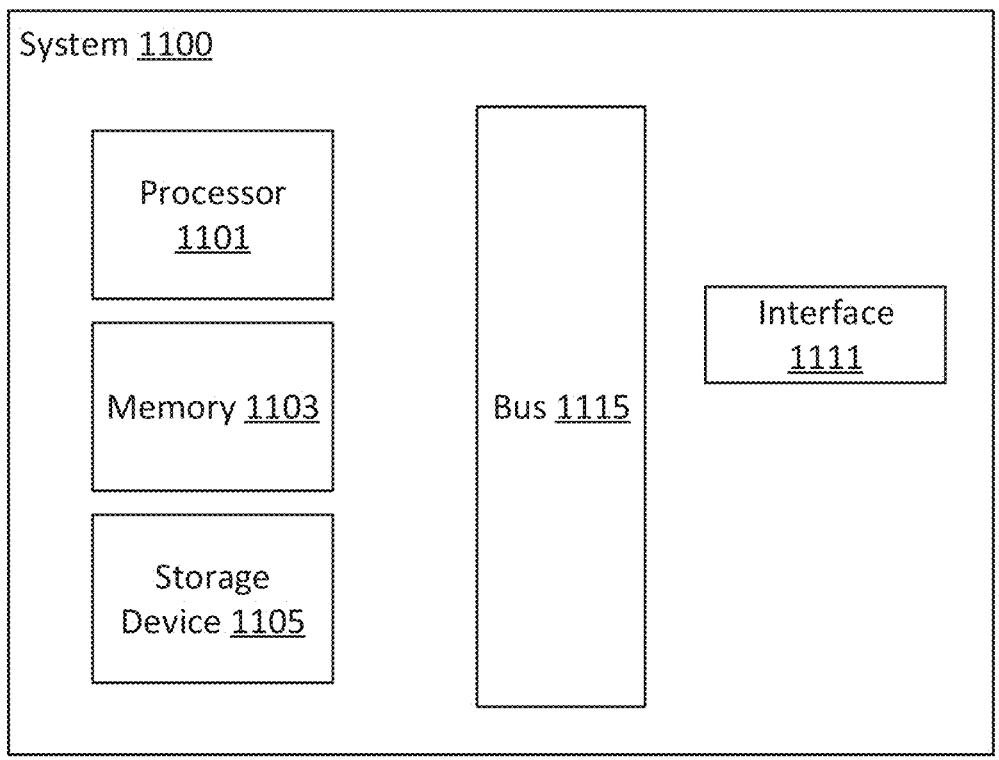
FIG. 11 illustrates one example of a computing device, configured in accordance with one or more embodiments.

FIG. 11 illustrates one example of a computing device, configured in accordance with one or more embodiments. According to various embodiments, a system 1100 suitable for implementing embodiments described herein includes a processor 1101, a memory module 1103, a storage device 1105, an interface 1111, and a bus 1115 (e.g., a PCI bus or other interconnection fabric.) System 1100 may operate as a variety of devices such as an application server, a database server, or any other device or service described herein. Although a particular configuration is described, a variety of alternative configurations are possible. The processor 1101 may perform operations such as those described herein. Instructions for performing such operations may be embodied in the memory 1103, on one or more non-transitory computer readable media, or on some other storage device. Various specially configured devices can also be used in place of or in addition to the processor 1101. The interface 1111 may be configured to send and receive data packets over a network. Examples of supported interfaces include, but are not limited to: Ethernet, fast Ethernet, Gigabit Ethernet, frame relay, cable, digital subscriber line (DSL), token ring, Asynchronous Transfer Mode (ATM), High-Speed Serial Interface (HSSI), and Fiber Distributed Data Interface (FDDI). These interfaces may include ports appropriate for communication with the appropriate media. They may also include an independent processor and/or volatile RAM. A computer system or computing device may include or communicate with a monitor, printer, or other suitable display for providing any of the results mentioned herein to a user.

Any of the disclosed implementations may be embodied in various types of hardware, software firmware, computer readable media, and combinations thereof. For example, some techniques disclosed herein may be implemented, at least in part, by computer-readable media that include program instructions, state information, etc., for configuring a computing system to perform various services and operations described herein. Examples of program instructions include both machine code, such as produced by a compiler, and higher-level code that may be executed via an interpreter. Instructions may be embodied in any suitable language such as, for example, Apex, Java, Python, C++, C, HTML, any other markup language, JavaScript, ActiveX, VBScript, or Perl. Examples of computer-readable media include, but are not limited to: magnetic media such as hard disks and magnetic tape; optical media such as flash memory, compact disk (CD) or digital versatile disk (DVD); magneto-optical media; and other hardware devices such as read-only memory ("ROM") devices and random-access memory ("RAM") devices. A computer-readable medium may be any combination of such storage devices.

In the foregoing specification, various techniques and mechanisms may have been described in singular form for clarity. However, it should be noted that some embodiments include multiple iterations of a technique or multiple instantiations of a mechanism unless otherwise noted. For example, a system uses a processor in a variety of contexts but can use multiple processors while remaining within the scope of the present disclosure unless otherwise noted. Similarly, various techniques and mechanisms may have been described as including a connection between two entities. However, a connection does not necessarily mean a direct, unimpeded connection, as a variety of other entities (e.g., bridges, controllers, gateways, etc.) may reside between the two entities.

In the foregoing specification, reference was made in detail to specific embodiments including one or more of the best modes contemplated by the inventors. While various implementations have been described herein, it should be understood that they have been presented by way of example only, and not limitation. For example, some techniques and mechanisms are described herein in the context of on-demand computing environments that include MTSs. However, the techniques of disclosed herein apply to a wide variety of computing environments. Particular embodiments may be implemented without some or all of the specific details described herein. In other instances, well known process operations have not been described in detail in order to avoid unnecessarily obscuring the disclosed techniques. Accordingly, the breadth and scope of the present application should not be limited by any of the implementations described herein, but should be defined only in accordance with the claims and their equivalents.

The invention claimed is:

1. A method comprising:
receiving, via a database system, one or more enrollment messages including identification information associated with a designated person, the one or more enrollment messages further including contact information identifying one or more individuals with which the designated person has recently come into physical proximity;
identifying health status information indicating a presence or absence of one or more medical symptoms associated with the designated person based on information included in the one or more enrollment messages;
generating a visual representation of a contact tracing graph for presentation on a user interface using the health status information and the contact information in the one or more enrollment messages, the contact tracing graph including the designated person and identifying one or more individuals with which the designated person has recently come into physical proximity;
receiving, via the visual representation, a selection of a first individual in the one or more individuals;
determining enrollment information for the first individual, wherein the enrollment information includes health status information for the first individual;
changing displayed information in the visual representation based on the health status information;
processing information for the visual representation select a second individual on the visual representation, wherein the second individual is selected based on the visual representation that was changed and prioritization information associated with the contact tracing graph; and providing an aid to select the second individual on the visual representation.

2. The method recited in claim 1, wherein the one or more enrollment messages include a calendar import message in which one or more calendar events are imported from a digital calendar associated with the designated person, and where a first one of the individuals is identified by being included in one of the calendar events.

3. The method recited in claim 1, wherein the one or more enrollment messages include a chat bot communication message in which the designated person communicates with a chat bot via one or more text message, and wherein a database record is created based at least in part on natural language processing performed on the chat bot communication message.

4. The method recited in claim 1, wherein a time, a date, a location, and a type of action associated with the physical proximity is associated with the one or more individuals.

5. The method recited in claim 1, wherein the visual representation of the contact tracing graph is presented in a user interface that facilitates communication with and enrollment of the individuals with whom the designated person has recently come into physical proximity.

6. The method recited in claim 1, wherein the database system is accessible via an on-demand computing services environment providing computing services to a plurality of organizations, and wherein database records for the contact tracing graph are associated with a designated one of the plurality of organizations.

7. The method recited in claim 1, wherein the database system is a multi-tenant database system configured to store information associated with a plurality of organizations, and wherein database records for the contact tracing graph are associated with a designated one of the plurality of organizations.

8. A system configured to perform a method, the method comprising:
receiving, via a database system, one or more enrollment messages including identification information associated with a designated person, the one or more enrollment messages further including contact information identifying one or more individuals with which the designated person has recently come into physical proximity;
identifying health status information indicating a presence or absence of one or more medical symptoms associated with the designated person based on information included in the one or more enrollment messages;
generating a visual representation of a contact tracing graph for presentation on a user interface using the health status information and the contact information in the one or more enrollment messages, the contact tracing graph including the designated person and identifying one or more individuals with which the designated person has recently come into physical proximity;
receiving, via the visual representation, a selection of a first individual in the one or more individuals;
determining enrollment information for the first individual, wherein the enrollment information includes health status information for the first individual;
changing displayed information in the visual representation based on the health status information;
processing information for the visual representation select a second individual on the visual representation, wherein the second individual is selected based on the visual representation that was changed and prioritization information associated with the contact tracing graph; and
providing an aid to select the second individual on the visual representation.

9. The system recited in claim 8, wherein the one or more enrollment messages include a calendar import message in which one or more calendar events are imported from a digital calendar associated with the designated person, and where a first one of the individuals is identified by being included in one of the calendar events.

10. The system recited in claim 8, wherein the one or more enrollment messages include a chat bot communication message in which the designated person communicates with a chat bot via one or more text message, and wherein a first database record is created based at least in part on natural language processing performed on the chat bot communication message.

11. The system recited in claim 8, wherein a time, a date, a location, and a type of action associated with the physical proximity is associated with the one or more individuals.

12. The system recited in claim 8, wherein the visual representation of the contact tracing graph is presented in a user interface that facilitates communication with and enrollment of the individuals with whom the designated person has recently come into physical proximity.

13. The system recited in claim 8, wherein the database system is accessible via an on-demand computing services environment providing computing services to a plurality of organizations, and wherein database records for the contact tracing graph are associated with a designated one of the plurality of organizations.

14. The system recited in claim 8, wherein the database system is a multi-tenant database system configured to store information associated with a plurality of organizations, and wherein database records for the contact tracing graph are associated with a designated one of the plurality of organizations.

15. One or more non-transitory computer readable media having instructions stored thereon for performing a method, the method comprising:
receiving, via a database system, one or more enrollment messages including identification information associated with a designated person, the one or more enrollment messages further including contact information identifying one or more individuals with which the designated person has recently come into physical proximity;
identifying health status information indicating a presence or absence of one or more medical symptoms associated with the designated person based on information included in the one or more enrollment messages;
generating a visual representation of a contact tracing graph for presentation on a user interface using the health status information and the contact information in the one or more enrollment messages, the contact tracing graph including the designated person and identifying one or more individuals with which the designated person has recently come into physical proximity;
receiving, via the visual representation, a selection of a first individual in the one or more individuals;

determining enrollment information for the first individual, wherein the enrollment information includes health status information for the first individual;

changing displayed information in the visual representation based on the health status information;

processing information for the visual representation select a second individual on the visual representation, wherein the second individual is selected based on the visual representation that was changed and prioritization information associated with the contact tracing graph; and providing an aid to select the second individual on the visual representation.

16. The one or more non-transitory computer readable media recited in claim 15, wherein the one or more enrollment messages include a calendar import message in which one or more calendar events are imported from a digital calendar associated with the designated person, and where a first one of the individuals is identified by being included in one of the calendar events.

17. The one or more non-transitory computer readable media recited in claim 15, wherein the one or more enrollment messages include a chat bot communication message in which the designated person communicates with a chat bot via one or more text message, and wherein a first database record is created based at least in part on natural language processing performed on the chat bot communication message.

18. The one or more non-transitory computer readable media recited in claim 15, wherein a time, a date, a location, and a type of action associated with the physical proximity is associated with the one or more individuals.

19. The one or more non-transitory computer readable media recited in claim 15, wherein the visual representation of the contact tracing graph is presented in a user interface that facilitates communication with and enrollment of the individuals with whom the designated person has recently come into physical proximity.

20. The one or more non-transitory computer readable media recited in claim 15, wherein the database system is accessible via an on-demand computing services environment providing computing services to a plurality of organizations, and wherein database records for the contact tracing graph are associated with a designated one of the plurality of organizations.

* * * * *